US005260281A

United States Patent [19]

Pittarelli et al.

[11] Patent Number: 5,260,281

[45] Date of Patent: Nov. 9, 1993

[54] BIOLOGICAL PESTICIDE DERIVED FROM NICOTIANA PLANTS

[75] Inventors: George W. Pittarelli, Hyattsville; Joseph G. Buta, Beltsville; John W. Neal, Jr., Laurel; William R. Lusby, Adelphi; Rolland M. Waters, Gaithersburg, all of Md.

[73] Assignee: The United States of America as represented by the Secretary of Agriculture, Washington, D.C.

[21] Appl. No.: 877,507

[22] Filed: May 1, 1992

[51] Int. Cl.[5] ...................... A01N 25/00; C08B 37/00; A61K 31/715; A61K 35/78

[52] U.S. Cl. .................................... 514/53; 536/1.11; 536/123.13; 536/127; 536/128; 424/197.1; 424/405

[58] Field of Search ............... 514/53; 424/405, 197.1; 536/1.11, 123.13, 127, 128

[56] References Cited

U.S. PATENT DOCUMENTS

| | | | |
|---|---|---|---|
| 2,007,123 | 7/1935 | Dunn | 424/197.1 |
| 4,520,020 | 5/1985 | Loebenstein et al. | 424/197.1 |
| 4,943,563 | 7/1990 | Mutschler et al. | 514/23 |

OTHER PUBLICATIONS

Jackson et al., "Journal of Chemical Ecology," vol. 17, No. 12, 1991, pp. 2489–2506.

Kandra et al., "Plant Physiol." (1990), vol. 94, pp. 906–912.

Burk et al., *Journal of Economic Entomology*, vol. 62(5), pp. 1115–1117 (1969).

Patterson et al., *Journal of Economic Entomology*, vol. 67(3), pp. 341–343 (1973).

Thurston et al., *Ent. Exp. & Appl.*, vol. 5, pp. 233–238 (1962).

Severson et al., *Plant Growth Assay* pp. 175–186.

Johnson et al., *Tobacco Science*, vol. 26, pp. 98–102 (1982).

Jones et al., *Entomol. Exp. Appl.*, vol. 38, pp. 157–164 (1985).

Severson et al., *J. Agric. Food Chem.*, vol. 33, pp. 870–875 (1985).

Cutler et al., in *Natural Resistance of Plants to Pests*, American Chemical Society Publication, pp. 178–195 (1986).

Wahlberg et al., *Acta Chemical Scandinavia*, vol. B40(9), pp. 724–730 (1986).

Kabara, J. J., *ACS Symposium Series*, N. 325, pp. 220–238 (1987).

Neal et al., *Tob. Int.*, vol. 189(15), p. 94 (1987) and *Tob. Sci.*, vol. 31, pp. 61–62 (1987).

Arrendale et al., *J. Agr. Food Chem.*, vol. 38(1), pp. 75–85 (1990).

*Primary Examiner*—Ronald W. Griffin

*Attorney, Agent, or Firm*—Janelle S. Graeter; M. Howard Silverstein

[57] ABSTRACT

Specific sucrose esters have been found to act as effective, environmentally-safe pesticides against soft-bodied arthropod plant pests. These compounds have acyl substituents having up to 10 carbon atoms and are easily extractable from Nicotiana plants. The compounds are used as a mixture, as extracted from the plants, and are spray-applied as an emulsion in water.

21 Claims, No Drawings

BIOLOGICAL PESTICIDE DERIVED FROM NICOTIANA PLANTS

FIELD OF THE INVENTION

This invention relates to novel, naturally-occurring, biologically active compounds extractable from plant leaves of Nicotiana species and to their use as effective, environmentally-safe pesticides. In addition, a pesticide composition and a method of using the composition are also disclosed. The novel compounds are specific sucrose esters and are capable of controlling arthropod plant pests such as aphids, mites and whiteflies. The compounds are applied as a mixture in an emulsion in water, utilizing either a crude extract or a chromatographically purified preparation. The use of these compounds results in a decrease in damage due to insect feeding, in the potential transfer of plant pathogenic viruses and in the formation of favorable environments for the development of sooty molds.

BACKGROUND OF THE INVENTION

Arthropod plant pests cause extensive and severe damage to major agricultural commodities, both in the field and in the greenhouse environment. In addition to feeding damage, many of these insects also transmit viral diseases, and insects such as whiteflies and aphids deposit "honey dew" on leaves, thus providing a favorable environment for the production of sooty mold which reduces photosynthetic activity and crop quality.

Infestation by the new B strain of the sweetpotato whitefly has proven particularly devastating to growers from Florida to California and as far north as New York and Ohio. The insect has a wide host range which includes over 500 species of plants. Two dissimilar species, the greenhouse whitefly and sweetpotato whitefly, alone have caused economically significant damage to poinsettia, hibiscus, tomato, crossandra and other plants in a greenhouse environment. The greenhouse whitefly, native to North America, is now world wide in distribution and is resistant to most synthetic pesticides. The sweetpotato whitefly is not limited to the greenhouse environment and is particularly difficult to control on row crops because it develops on the lower leaf surface which is difficult to adequately cover with pesticides. It also has the ability to change host plant and to acquire resistance to conventional chemical pesticides. The recent rapid spread of strain B of this whitefly has caused significant economic losses to growers of cotton, melons, squash, sugar beets, lettuce, carrots, tomatoes, peanuts, alfalfa and ornamental plants. In addition, it is a vector for more than 70 diseases including 25 viruses, and, following serious whitefly infestations, several agricultural regions have been subjected to the viral diseases which cause pepper necrosis and yellowing of lettuce.

Whiteflies are generally tropical in distribution, however the sweetpotato whitefly is now believed to have spread in the United States with impunity because of a high level of insecticide resistance and insignificant natural enemies. There have been some efforts to establish populations of parasitoids which apparently reduce or suppress the insect in its native habitat.

Chemical control of whiteflies has proven difficult for several reasons. The insect has a complex life cycle where the egg and pupal stages are generally resistant to chemicals. The entire life cycle is very short (approximately one month), resulting in a rapid increase in population. A severe infestation often occurs before a grower recognizes the problem, making eradication even more difficult. The infestations are rarely localized since the adult readily flies and the immature stages are distributed on bedding and ornamental plants. It can also develop a resistance to chemical insecticides fairly quickly, requiring control methods utilizing an alternating schedule of chemicals.

In choosing an effective pesticide, the mode of action is an important factor. The whitefly uses a piercing and sucking system to extract food from the phloem of the infested plant, and its stylets can penetrate through a dry film of pesticide on plant tissue without serious consequence from the pesticide. Therefore, either a systemic pesticide which penetrates the leaf surface or is absorbed by the roots and can be ingested by the insect or one which penetrates or acts directly on the insect are the limited approaches.

Long chain fatty acids (particularly $C_{12}$) and fatty acid soaps have been reported as effective in the control of insects (Kabara, ACS Symposium Series, No. 325, 1987). In addition, various species of Nicotiana plants have been shown to have resistance to infestation by green peach aphids (Thurston et al., *Ent. Exp. & Appl.*, 1962 and Burk et al., *J. of Econ. Ent.*, 1969), two-spotted spider mites (Patterson et al., *J. of Econ. Ent.*, 1974), tobacco hornworm (Jones et al., *Entomol. Exp. Appl.*, 1985) and greenhouse whitefly (Neal et al., *Tob. Int.*, 1987). Moreover, Cutler et al. (in *Natural Resistance of Plants to Pests*, American Chemical Society, 1986) studied leaf surface chemicals of *N. tabacum* and suggested that plant resistance to tobacco budworm is associated with the presence of a mixture of sucrose esters having an acetate group at the $C_6$ position of the glucose moiety and a series of $C_3$ to $C_8$ alkanoyl groups, in particular 2-methylbutyrate and 3-methylvalerate. Johnson et al. (*Tobacco Science*, 1982) also studied tobacco leaf surface chemistry to determine the cause of plant resistance to aphids and found that high levels of sucrose esters or duvatriene-ols appeared to be responsible. The need therefore exists for the identification and development of the particular specific sucrose esters present in Nicotiana leaves which have the capability of controlling soft-bodied arthropod insect pests.

SUMMARY OF THE INVENTION

We have now discovered the new and novel sucrose esters Which meet the requirement of providing effective pesticidal activity against soft-bodied arthropod plant pests. These compounds are natural products which biodegrade into innocuous compounds, thereby avoiding chemical contamination of the environment. Accordingly, it is an object of the invention to provide specific naturally-occurring sucrose esters having acyl substituents ($C_1$–$C_{10}$) on both the fructose and glucose moieties, the compounds being extractable from the leaves of Nicotiana plants.

It is a further object of the invention to provide a pesticide composition comprising the novel naturally-occurring compounds in a pesticidally effective amount. To meet this objective, an emulsion of the active compounds in water is provided for spray application to the target pests.

Another object of the invention is to provide a method of treating soft-bodied arthropod plant pests by administering effective amounts of the pesticide composition to areas suspected of infestation.

Other objects and advantages of the invention will become readily apparent from the following description.

DETAILED DESCRIPTION OF THE INVENTION

The primary novel feature of the invention provides novel compounds derived from Nicotiana plants and having the structure:

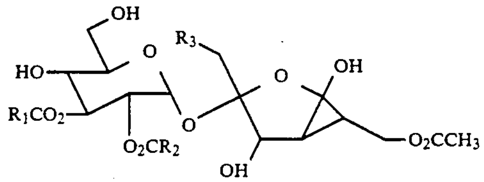

wherein $R_1$ and $R_2$ are each straight chain or branched aliphatic alkyl groups having from one to ten carbon atoms, and $R_3$ is —OH or —$O_2CCH_3$. Preferably, $R_1$ and $R_2$ are the same are 4-methylhexyl or are different and are interchangeably 4-methylpentyl and 4-methylhexyl. The compounds were identified using mass spectrometry and nuclear magnetic resonance techniques following extraction and purification procedures. While the substituents at the $R_1$, $R_2$ and $R_3$ position may vary, it is critical to the effectiveness of the invention that the remaining acyl group (—$O_2CCH_3$) on the fructose moiety remain constant.

The compounds may be extracted from Nicotiana leaves by immersion in a polar organic solvent, preferably methylene chloride, for a short period of time, preferably about one minute. The solvent is removed by evaporation at about 25° C. The residue of crude extract may be used, or it may be further purified by conventional means such as chromatographic procedures. Preferably, gel permeation chromatography followed by silica chromatography, as described by Buta et al., ACS Symposium Series, No. 380, 1988, and Matsuzaki et al., *Agric. Biol. Chem.*, 1989, both herein incorporated by reference, are utilized.

The compounds are not separated for use, but are preferably used as a mixture as extracted from the plant. The extract forms a stable emulsion in water and is very active at ambient temperature. Crude extract may be used at a concentration of about 0.5% to about 1.5% (w/v), preferably about 1.0% (w/v), while purified product may be used at lower concentrations such as about 0.1% to about 0.2% (w/v).

An active emulsion may be applied in high volume by a conventional sprayer at ambient temperature. It may be applied directly to the leaf surface where it can act as a repellant for certain pests, such as mites, by functioning as a deterrent to feeding by the adult mite and by inhibiting ovipositioning. It may also be applied directly to pests, which is followed by rapid collapse and dessication. It is also effective in preventing whitefly nymphs from becoming adults, thereby interrupting the growth/life cycle.

The novel compounds of the invention may be extracted from a variety of Nicotiana plant species, including *N. gossei, N. benthamiana, N. cavicola, N. bigelovii, N. kawakamii, N. trigonophylla, N. fragrans, N. glutinosa, N. repanda, N. langsdorffii, N. benavidesii* and *N. tabacum.* Preferred species are *N. gossei, N. benthamiana* and *N. cavicola,* While the particularly preferred species is *N. gossei.* While naturally-occurring compounds are described, synthetic compounds would also be considered effective active agents.

Target pests for which the novel compounds are effective include soft-bodied arthropod insects. Particularly susceptible are mites such as spider mites, aphids, whiteflies and whitefly nymphs, adelgids, psyllids, scale crawlers, mealybugs and thrips. Of particular interest are mites, whiteflies and aphids. In addition, the compounds are effective for the protection of any host plant susceptible to infestation by these soft-bodied arthropod plant pests. Ornamental plants such as poinsettias, hibiscus and roses and row crops such as melons, tomatoes, broccoli, lettuce and cotton are examples of the variety of plants which may benefit.

The following examples are intended only to further illustrate the invention and are not intended to limit the scope of the invention as defined by the claims.

EXAMPLES

Example 1

Extraction of Sucrose Esters from *N. gossei*

*N. gossei* plants were grown in a greenhouse environment to the blooming stage. Mature, fully expanded leaves were harvested, and 600 ml of methylene chloride was used to rinse the surfaces of 400 g of harvested leaves. The solvent was removed by rotary evaporation at 30° C., leaving a residue of crude extract.

For chromatographic purification, the residue was partitioned between 80 ml hexane and 80 ml 80% aqueous methanol. The lower aqueous phase was then partitioned against a mixture of 33 ml saturated KCl, 50 ml $H_2O$ and 100 ml methylene chloride. The lower methylene chloride layer was taken to dryness by rotary evaporation, as described, and the resulting residue dissolved in ethyl acetate. Fractionation on a Bio-Beads S-X2 column (2.5 cm ×32 cm) using 120 ml of ethyl acetate was carried out. Ten fractions were collected, 3×20 ml followed by 7×10 ml. Fractions 6 and 7 were combined, concentrated and placed on a silica gel 60 column (1.0 cm×16 cm). The column was sequentially eluted with 40 ml each ethyl acetate, 1% methanol in ethyl acetate, 5% methanol in ethyl acetate followed by 20 ml 10% methanol in ethyl acetate. Ten-ml fractions were collected. Fractions 7 and 8 were combined and reduced to dryness.

Example 2

Evaluation of Crude Extract from Nicotiana Against Greenhouse Whitefly Nymphs Tomato plants were exposed for 48 hours to an environment having a high population of greenhouse whitefly (GHWF) adults, then removed in order to ensure a high number of synchronized instars. Crude surface extract, described in Example 1, was prepared as an emulsion in water (1%) and spray-applied to second instar GHWF under normal greenhouse conditions. Three leaflets with a high number of second instars were sprayed to runoff with extract from each test species. In a single multiple species comparison test, fourteen different Nicotiana species were evaluated. The test was repeated three times. Safer's soap (1%) solution and water were used as positive and negative controls, respectively. Leaf discs (3.65 cm$^2$) were cut from each leaflet, and counts were made of live and dead whiteflies at the time of adult emergence and converted to mean percent mortality (Table 1). Mortalities ranged from 100% for extract from *N. gossei* to 4% for extract from *N. rustica*, indicating that there are higher amounts of the critical compounds present in some species than others.

Example 3

Evaluation of Silica Column Preparation of Sucrose Esters from *N. gossei* against Green Peach Aphids Sucrose esters were extracted from *N. gossei* and chromatographically purified as described in Example 1. A 0.1% emulsion in water was prepared and utilized for the treatment of green peach aphids. Young ovoviviparous females of the green peach aphid were selected and transferred from a colony

TABLE 1

Effects of Crude Extracts from Nicotiana Species on Greenhouse Whitefly Nymphs

| Nicotiana Species | Percent Mortality | Nicotiana Species | Percent Mortality |
|---|---|---|---|
| *N. gossei* | 100 | *N. langsdorffii* | 37 |
| *N. bigelovii* | 77 | *N. benavidesii* | 19 |
| *N. kawakamii* | 54 | *N. tabacum*, KY 16 | 19 |
| *N. trigonophylla* | 52 | *N. nudicaulis* | 09 |
| *N. fragrans* | 42 | *N. undulata* | 05 |
| Safers Soap (1%) | 37 | *N. noctiflora* | 05 |
| *N. glutinosa* | 48 | $H_2O$ | 04 |
| *N. repanda* | 36 | *N. rustica* | 04 |

maintained on *N. tabacum* to the abaxial surface of excised leaves of *N. tabacum*, each having been maintained upright in a bottle of water.

Two tests were performed. For each test, the sucrose ester emulsion was applied as a fine spray to runoff to the infested leaf surface and air-dried. Water was applied as a negative control in each test, and a Safer's soap solution (2%) was applied as a positive control in the second test. Petri dishes (60 mm×15 mm) containing untreated leaf discs (1.45 $cm^2$) of *N. tabacum* resting on wet filter paper were set up so that each dish contained one disc for each treatment. In test one, there were 20 Petri dishes per treatment, in test two there were 10. In test one, a single treated female was transferred to each disc and allowed to feed and reproduce for 72 hours. At the end of the 72-hour period, counts were made of both the number of living females and the number of progeny. In the second test, five aphids were placed on each disc and observed for mortality at 24 hours.

Results of test one are shown in Table 2. In each test, most of the aphids treated with *N. gossei* extract were dead at the time the leaf surface was considered air-dried. The water negative control showed numerous live females and progeny, as expected. In the second test, aphids that were treated with the 2% Safer's soap as a positive control were also dead at the air-dry condition (results not shown in Table).

TABLE 2

Effect of Sucrose Esters from *N. gossei* on Green Peach Aphids.

| Treatment | Number Alive | |
|---|---|---|
| | Females | Progeny |
| *N. gossei* | 2 | 0 |
| $H_2O$ | 19 | 65 |

Example 4

Evaluation of the Effects of Silica Column Preparation of Sucrose Esters from *N. gossei* on Oviposition and Mortality of Twospotted Spider Mites Sucrose esters were extracted from *N. gossei* and chromatographically purified as described in Example 1. A 0.2% emulsion in water was prepared and applied as a fine spray on eggplant leaves to a wet condition either to the abaxial surface only or to both surfaces, followed by air drying. Ten discs (3.22 $cm^2$) from each treated leaf and ten from an untreated leaf were cut and individually placed on a Petri dish (60 mm×15 mm), abaxial side up on wet filter paper. Five migratory females from a colony of twospotted spider mites were place on each disc for a period of 72 hours. At the end of the 72-hour period, counts were made of the number of live females and the number of eggs. The results are presented in Table 3. It can be seen that the extract is more effective with respect to oviposition than mortality, although approximately one-half of the population was found dead, especially those on leaves which had been treated on both sides.

TABLE 3

Effect of Sucrose Esters from *N. gossei* on Oviposition and Mortality of Twospotted Spider Mites.

| Treatment: | No. of Eggs | | Female % Mortality | |
|---|---|---|---|---|
| | Test 1 | Test 2 | Test 1 | Test 2 |
| Single side | 18 | 4 | 38 | 60 |
| Double side | 2 | 1 | 52 | 60 |
| Untreated | 555 | 244 | 28 | 4 |

We claim:

1. A compound having the structure

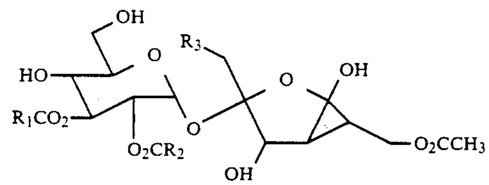

wherein $R_1$ and $R_2$ are each independently aliphatic groups which are straight chain or branched alkyl chains having 1 to 10 carbon atoms and $R_3$ is —OH or —$O_2CCH_3$.

2. The compound of claim 1, wherein both $R_1$ and $R_2$ are 4-methylhexyl.

3. The compound of claim 1, wherein both $R_1$ and $R_2$ are 4-methylpentyl.

4. The compound of claim 1, wherein $R_1$ and $R_2$ are different and are interchangeably 4-methylhexyl and b 4-methylpentyl.

5. The compound of claim 1, wherein $R_1$ is 4-methylhexyl, $R_2$ is 4-methylpentyl and $R_3$ is —OH.

6. The compound of claim 1, wherein $R_1$ is 4-methylpentyl, $R_2$ is 4-methylhexyl and $R_3$ is —OH.

7. The compound of claim 1, wherein both $R_1$ and $R_2$ are 4-methylhexyl and $R_3$ is —OH.

8. The compound of claim 1, wherein $R_1$ is 4-methylhexyl, $R_2$ is 4-methylpentyl and $R_3$ is —$O_2CCH_3$.

9. The compound of claim 1, wherein $R_1$ is 4-methylpentyl, $R_2$ is 4-methylhexyl and $R_3$ is —$O_2CCH_3$.

10. The compound of claim 1, wherein both $R_1$ and $R_2$ are 4-methylhexyl and $R_3$ is —$O_2CCH_3$.

11. The compound of claim 1, wherein both $R_1$ and $R_2$ are 4-methylpentyl and $R_3$ is $—O_2CCH_3$.

12. A pesticide composition effective for treating soft-bodied arthropod plant pests comprising an effective amount of a mixture of sucrose ester compounds having the structure

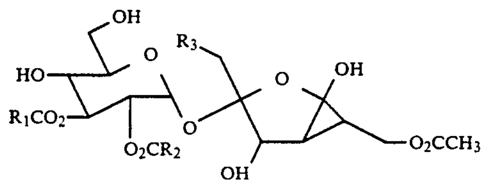

wherein $R_1$ and $R_2$ are each independently aliphatic groups which are straight chain or branched alkyl chains having 1 to 10 carbon atoms and $R_3$ is —OH or $—O_2CCH_3$.

13. The composition of claim 12 comprising a mixture of compounds where $R_1$ is 4-methylhexyl, $R_2$ is 4-methylpentyl and $R_3$ is —OH; $R_1$ is 4-methylpentyl, $R_2$ is 4-methylhexyl and $R_3$ is —OH; $R_1$ and $R_2$ are both 4-methylhexyl and $R_3$ is —OH; $R_1$ is 4-methylhexyl, $R_2$ is 4-methylpentyl and $R_3$ is $—O_2CCH_3$; $R_1$ is 4-methylpentyl and $R_3$ is $—O_2CCH_3$; $R_1$ is 4-methylpentyl, $R_2$ is 4-methylhexyl and $R_3$ is $—O_2CCH_3$; $R_1$ and $R_2$ are both 4-methylhexyl and $R_3$ is $—O_2CCH_3$; and $R_1$ and $R_2$ are both 4-methylpentyl and $R_3$ is $—O_2CCH_3$.

14. The composition of claim 12, wherein said sucrose ester compounds are extracted from species of Nicotiana plants and used in the composition as a crude extract.

15. The composition of claim 14, wherein said crude extract is chromatographically treated to produce purified sucrose ester compounds.

16. The composition of claim 14, wherein the concentration of sucrose ester compounds is about 0.5 to about 1.5% (w/v).

17. The composition of claim 16, wherein said concentration is about 1.0% (w/v).

18. The composition of claim 15, wherein the concentration of sucrose ester compounds is about 0.1% to about 0.2% (w/v).

19. The composition of claim 12, wherein the sucrose ester compounds are emulsified in water.

20. A method of treating soft-bodied arthropod plant pests by administering effective amounts of the pesticide composition of claim 12 to areas suspected of infestation.

21. A method of claim 20, wherein said soft-bodied arthropod plant pests are mites, aphids, whiteflies, whitefly nymphs, adelgids, psyllids, scale crawlers, mealybugs and thrips.

* * * * *